United States Patent [19]

Ushikubo

[11] Patent Number: 5,227,482

[45] Date of Patent: Jul. 13, 1993

[54] METHOD FOR PRODUCING A LACTAM

[75] Inventor: Takashi Ushikubo, Yokohama, Japan

[73] Assignee: Mitsubishi Kasei Corporation, Tokyo, Japan

[21] Appl. No.: 870,316

[22] Filed: Apr. 17, 1992

[30] Foreign Application Priority Data

Apr. 17, 1991 [JP] Japan .................................. 3-085401

[51] Int. Cl.$^5$ .......................................... C07D 201/02
[52] U.S. Cl. ................................... 540/536; 540/535; 540/464; 546/243
[58] Field of Search ................. 540/535, 536, 464; 546/243

[56] References Cited

U.S. PATENT DOCUMENTS 4,717,770  1/1988  Sato et al. ............................ 540/536

FOREIGN PATENT DOCUMENTS 0135145  3/1985  European Pat. Off. ............ 540/536
0242960  10/1987  European Pat. Off. ............ 502/353
63-51945  3/1988  Japan .................................. 502/353
881927  11/1961  United Kingdom ............... 540/536

OTHER PUBLICATIONS

Patent Abstracts of Japan, vol. 12, No. 270(C-515)(3117), Jul. 27, 1988, & JP-A-63-051945, Mar. 5, 1988.

Primary Examiner—Robert T. Bond
Attorney, Agent, or Firm—Oblon, Spivak, McClelland, Maier & Neustadt

[57] ABSTRACT

A method for preparing a lactam, which comprises subjecting a cycloalkanone oxime to a Beckmann rearrangement reaction in a gas phase in the presence of a carrier-supported catalyst containing tantalum, wherein the carrier-supported catalyst is the one prepared by contacting an organic compound containing tantalum to a silica carrier having pores with pore diameters of from to 150,000 Å wherein the pore volume of pores with pore diameters of from 40 to 2,000 Å is at least 80% of the total pore volume of pores with pore diameters of from 40 to 150,000 Å.

9 Claims, No Drawings

METHOD FOR PRODUCING A LACTAM

The present invention relates to a method for producing a lactam. More particularly, it relates to a method for efficiently producing a lactam such as ε-caprolactam by subjecting a cycloalkanone oxime to a Beckmann rearrangement reaction in a gas phase.

A lactam is usually produced by a Beckmann rearrangement reaction of cycloalkanone oxime. As such a Beckmann rearrangement reaction, it is common for an industrial operation to employ a liquid phase reaction using a strong acid such as concentrated sulfuric acid or fuming sulfuric acid. However, in such a method, it is usually required to neutralize sulfuric acid with ammonia in order to separate the lactam, whereby there is a problem that a substantial amount of ammonium sulfate is produced as a by-product.

Under these circumstances, various studies have been made for a Beckmann rearrangement reaction using no sulfuric acid. As a prospective method, it is conceivable to conduct the Beckmann rearrangement reaction in a gas phase in the presence of a solid acid catalyst. As the solid acid catalyst, a silica-alumina catalyst (UK Patent No. 881,927), a solid phosphoric acid catalyst (UK Patent No. 881,276), a titania-boria catalyst (Japanese Examined Patent Publication No. 12125/1971), a boron-type catalyst (German Patent No. 10920, "Applied Catalysis" Vol. 29, p107 (1987)), a hydrated niobium oxide catalyst (Japanese Unexamined Patent Publication No. 44039/1985) or a high silica type zeolite catalyst ("Catalyst" Vol. 31, No. 2, p136 (1989)) has, for example, been proposed.

Further, also the present inventors have previously found that a hydrated tantalum oxide is useful as an excellent solid acid catalyst for a Beckmann rearrangement reaction (Japanese Unexamined Patent Publication No. 51945/1988).

However, in a method wherein such a solid acid catalyst is employed to conduct the Beckmann rearrangement reaction in a gas phase, side-reactions such as thermal decomposition and polymerization are likely to take place, and separation of by-products such as amines, amides, cyans and tar-like high boiling point substances, tends to be cumbersome, whereby it is hardly possible to obtain ε-caprolactam in a sufficient yield. Further, there is an additional problem that a drop of the catalytic activities with time is substantial due to e.g. evaporation of the catalyst component with time.

The present inventors have conducted extensive studies to solve the above problems and as a result, have unexpectedly found that a lactam can be obtained at a very high selectivity when an oxime is subjected to a Beckmann rearrangement reaction in a gas phase using as a catalyst the one having tantalum supported on a certain specific silica. The present invention has been accomplished on the basis of this discovery.

Thus, the present invention provides a method for preparing a lactam, which comprises subjecting a cycloalkanone oxime to a Beckmann rearrangement reaction in a gas phase in the presence of a carrier-supported catalyst containing tantalum, wherein the carrier supported catalyst is the one prepared by contacting an organic compound containing tantalum to a silica carrier having pores with pore diameters of from 40 to 150,000 Å wherein the pore volume of pores with pore diameters of from 40 to 2,000 Å is at least 80% of the total pore volume of pores with pore diameters of from 40 to 150,000 Å.

Now, the present invention will be described in detail with reference to the preferred embodiments.

The carrier for the solid catalyst to be used in the present invention is silica, particularly silica having a certain specific structure. Namely, when the pore size distribution is measured by a mercury injection method, the silica to be used has a total pore volume of pores with diameters of from 40 to 150,000 Å being usually from 0.1 to 5 cc/g, preferably from 0.2 to 3 cc/g, wherein the pore volume of pores with diameters of from 40 to 2,000 Å is at least 80%, preferably at least 90%, of the total pore volume. The absolute amount may be usually from 0.1 to 5 cc/g, preferably from 0.2 to 3 cc/g. Further, in the pore size distribution, the silica preferably has a peak of the pore size distribution within a range of from 100 to 600 Å in diameter.

The silica having such a structure may be prepared by various conventional methods by appropriately controlling the production conditions. However, commercial products having the desired pore size distribution may suitably be selected for use. Further, impurities such as aluminum, boron, alkali metals or alkaline earth metals may be present to such an extent that they are usually contained in commercially available silica products, without creating any particular problem.

As a method for supporting tantalum on the above specific silica, it is important that an organic compound containing tantalum is contacted to the silica. Here, the organic compound containing tantalum may, for example, be a tantalum alkoxide of the formula $Ta(OR)_5$ wherein R is at least one member selected from the group consisting of a $C_{1-8}$ alkyl group, an alkenyl group and an aryl group, such as $Ta(OC_2H_5)_5$, $Ta(OC_3H_7)_5$ or $Ta(OC_4H_9)_5$; a tantalum alkoxide containing halogen, such as $TaCl(OCH_3)_4$ or $TaCl_2(OCH_3)_3$; or a tantalum organic acid salt such as tantalum oxalate, tantalum tartarate or tantalum ammonium oxalate.

As the contacting method, it is possible to employ a method wherein the organic compound containing tantalum is contacted to silica in the form of a solution dissolved in a solvent or in the form of a vapor. For example, in the case of a tantalum alkoxide, it is possible to employ a method wherein thoroughly dried silica is added to a solution of a tantalum alkoxide in a solvent such as hexane, heptane, octane or benzene, and the mixture is then left to stand still under atmospheric pressure at room temperature or at an elevated temperature, or a method wherein a vapor of a tantalum alkoxide is contacted to silica under atmospheric pressure at a temperature of from room temperature to 500° C., preferably from 100° to 400° C. After such contact treatment, the silica is usually washed with a solvent and dried, followed by calcining at a high temperature of from 200° to 600° C. to obtain a catalyst. The catalyst thus obtained is molded or granulated to have a suitable particle size and shape depending upon the scale or the manner of the reaction. In such a catalyst, tantalum is believed to be supported in the form of an oxide, and the supported amount is usually from 1 to 30 wt %, preferably from 3 to 20 wt %, as the oxide ($Ta_2O_5$) based on the entire amount ($Ta_2O_5$+silica).

The method of the present invention comprises subjecting a cycloalkanone oxime to the Beckmann rearrangement reaction by a gas phase contact by means of the above described catalyst.

The cycloalkanone oxime as the starting material for the reaction may usually be the one having from 5 to 12 carbon atoms. For the industrial purpose, cyclohexanone oxime having 6 carbon atoms is particularly useful. The purity of the starting material for the reaction is not required to be high and may be at a level commonly employed in an industrial operation by a sulfuric acid method.

The reaction is conducted by means of a reactor of e.g. a fixed bed system or a fluidized bed system. The cycloalkanone oxime may be introduced alone into the reactor. However, it is common to introduce it together with a carrier gas. The carrier gas may be a gas inert to the Beckmann rearrangement reaction, such as nitrogen, helium or argon, or in some cases, hydrogen, carbon dioxide or steam. These gases may be used alone or in combination as a gas mixture. Further, the cycloalkanone oxime may be supplied as dissolved in a solvent inert to the reaction, such as benzene or toluene. When a carrier gas is employed, the concentration of the cyclohexanone oxime vapor is usually from 0.5 to 40% by volume, preferably from 2 to 20% by volume, although such a concentration may suitably be selected depending upon the reaction conditions.

The reaction temperature is usually from 170° to 400° C., preferably from 250° to 380° C. Further, the reaction is usually conducted under atmospheric pressure, but can be conducted under a slightly elevated pressure or under a reduced pressure. Further, the gas space velocity SV in the gas phase reaction is usually within a range of from 100 to 20,000 hr$^{-1}$, preferably from 1,000 to 10,000 hr$^{-1}$, but the reaction is conducted so that the contact time of the cycloalkanone oxime vapor with the catalyst is usually from 0.01 to 3 seconds, preferably from 0.1 to 2 seconds.

Now, the present invention will be described in further detail with reference to Examples. However, it should be understood that the present invention is by no means restricted to such specific Examples.

In the following Examples, cyclohexanone oxime will be referred to simply as "oxime", and ε-caprolactam will be referred to simply as "lactam".

Physical properties of silica carriers

Silica carriers A to F used in the Examples are all commercial products (manufactured by Fuji Davison Chemical Company). In Table 1, the physical properties of silica carriers A to F are shown.

TABLE 1

| Silica carrier | Total pore volume ① (cc/g) | Pore volume of fine pores ② (cc/g) | (②/①) × 100 (%) | Peak of pore diameter (Å) | Specific surface area (m²g) |
|---|---|---|---|---|---|
| A | 0.847 | 0.833 | 98.4 | 154 | 240 |
| B | 1.032 | 1.022 | 99.0 | 340 | 111 |
| C | 1.072 | 1.059 | 98.8 | 540 | 93 |
| D | 0.767 | 0.718 | 93.6 | No distinct peak | 330 |
| E | 0.833 | 0.254 | 30.5 | No distinct peak | 25 |
| F | 0.241 | 0.170 | 70.5 | 50 | 173 |

Total pore volume ①: Total pore volume of pores with pore diameters of from 40 to 150,000 Å
Pore volume of fine pores ②: Pore volume of pores with pore diameters of from 40 to 2,000 Å

EXAMPLE 1

Silica carrier A identified in Table 1 was pulverized and sieved to obtain a carrier of from 16 to 28 mesh (from 0.59 to 0.9 mm), which was then evacuated at 100° C. for two hours. 10 ml of the carrier thus prepared was added to 100 ml of a hexane solution containing 1% by weight of tantalum penta-n-butoxide, and the mixture was left to stand at room temperature for 15 hours. Then, the mixture was subjected to filtration to remove the solution, and the residue was washed with hexane and dried under reduced pressure at 90° C. for 5 hours. Further, the product was subjected to heat treatment at 300° C. for two hours in a nitrogen stream and then at 300° C. for two hours in a dried air stream, to obtain a white tantalum-supporting catalyst. As a result of the elemental analysis, the supported amount of tantalum was 4.3 wt % as $Ta_2O_5$.

0.5 ml of the catalyst prepared as described above, was packed into a reaction tube, and a reaction gas with a volume ratio of oxime/benzene/$N_2$=4/42/52 was introduced at a reaction temperature of 300° C. at a space velocity SV of 4,800 hr$^{-1}$ to conduct the Beckmann rearrangement reaction. The reaction product was collected into cooled methanol and analyzed by gas chromatography. The results are shown in Table 2. After completion of the reaction for 10 hours, the catalyst withdrawn from the reaction tube was remained to be white, and no deposition of carbon was observed.

EXAMPLES 2 TO 4 AND COMPARATIVE EXAMPLES 1 AND 2

Catalysts were prepared in the same manner as in Example 1 except that silica carriers B to F as identified in Table 1 were used instead of silica carrier A in Example 1, and the reaction was conducted in the same manner. The results are shown in Table 2. In Examples 2 to 4, after completion of the reaction, no deposition of carbon to the catalysts was observed, and the conversion of oxime and the selectivity for lactam were maintained even upon expiration of the reaction time.

TABLE 2

| | Silica carrier | Supported amount of tantalum (wt %) | Time passed after initiation of reaction (hr) | Conversion of oxime (%) | Selectivity for lactam (%) | Yield of lactam |
|---|---|---|---|---|---|---|
| Example 1 | A | 4.3 | 1 | 96.5 | 97.5 | 94.1 |
| | | | 10 | 95.3 | 97.5 | 92.9 |
| Example 2 | B | 3.5 | 1 | 88.4 | 95.5 | 84.4 |
| | | | 10 | 85.7 | 95.5 | 81.8 |
| Example 3 | C | 2.8 | 1 | 81.0 | 95.5 | 77.4 |
| Example 4 | D | 6.2 | 1 | 88.7 | 92.2 | 81.8 |
| Comparative Example 1 | E | 3.4 | 1 | 72.8 | 72.5 | 52.8 |
| Comparative Example 2 | F | 6.7 | 1 | 53.6 | 72.5 | 38.9 |
| | | | 10 | 21.4 | 70.5 | 15.1 |

EXAMPLES 5 TO 9

Using the catalyst obtained in Example 1, a reaction was conducted under the reaction conditions as identified in Table 3. The results of the reaction upon expiration of one hour after the initiation of the reaction are shown in Table 3. In Example 9, toluene was used instead of benzene, and accordingly, the value in the column for benzene in Table 3 represents the amount of toluene.

EXAMPLE 10

The catalyst was prepared in the same manner as in Example 1 except that tantalum pentaethoxide was used instead of tantalum penta-n-butoxide in Example 1, and the reaction was conducted in the same manner. The results of the reaction upon expiration of one hour from the initiation of the reaction are shown in Table 3.

of one hour from the initiation of the reaction are shown in Table 4.

COMPARATIVE EXAMPLE 3

A catalyst was prepared in the same manner as in Example 1 except that the silica carrier was treated with a 1N hydrochloric acid aqueous solution containing 1% by weight of tantalum pentachloride instead of the hexane solution of tantalum penta-n-butoxide in Example 1 and washed with water instead of hexane, and the reaction was conducted in the same manner. The results of the reaction upon expiration of one hour from the initiation of the reaction are shown in Table 4.

TABLE 3

| Example No. | Supported amount of tantalum (wt %) | Reaction temp. (°C.) | Space velocity SV ($hr^{-1}$) | Gas composition (volume ratio) | | | Conversion of oxime (%) | Selectivity for lactam (%) | Yield of lactam (%) |
|---|---|---|---|---|---|---|---|---|---|
| | | | | Oxime | Benzene | Nitrogen | | | |
| 5 | 4.3 | 250 | 4800 | 4 | 42 | 54 | 57.3 | 96.5 | 55.3 |
| 6 | 4.3 | 350 | 4800 | 4 | 42 | 54 | 98.0 | 92.4 | 90.6 |
| 7 | 4.3 | 300 | 2400 | 4 | 42 | 54 | 97.7 | 94.6 | 92.4 |
| 8 | 4.3 | 300 | 4800 | 8 | 38 | 54 | 91.2 | 96.6 | 88.1 |
| 9 | 4.3 | 300 | 4800 | 4 | 42 | 54 | 94.4 | 96.0 | 90.6 |
| 10 | 8.5 | 300 | 4800 | 4 | 42 | 54 | 94.5 | 92.3 | 87.2 |

TABLE 4

| Example No. | Treating medium | Reaction temp. (°C.) | Supported amount of tantalum (wt %) | Conversion of oxime (%) | Selectivity for lactam (%) | Yield of lactam (%) |
|---|---|---|---|---|---|---|
| 11 | 2 wt % TB solution | Room temperature | 5.0 | 96.6 | 94.3 | 91.1 |
| 12 | 5 wt % TB solution | Room temperature | 9.5 | 97.8 | 94.4 | 92.3 |
| 13 | 1 wt % TB solution | 50 | 5.2 | 96.6 | 97.1 | 93.8 |
| 14 | TE vapor | 100 | 3.1 | 78.7 | 96.2 | 76.7 |
| Comparative Example 3 | 1 wt % tCl solution | Room temperature | 6.5 | 37.9 | 68.4 | 25.9 |

TB solution: Hexane solution of tantalum penta-n-butoxide
TE vapor: Vapor of tantalum pentaethoxide
TCl solution: 1N hydrochloric acid aqueous solution of tantalum pentachloride

EXAMPLES 11 TO 13

Catalysts were prepared in the same manner as in Example 1 except that the concentration of tantalum penta-n-butoxide or the treating temperature of silica in Example 1 was changed as identified in Table 4, and the reaction was conducted in the same manner. The results of the reaction upon expiration of one hour from the initiation of the reaction are shown in Table 4.

EXAMPLE 14

Silica carrier A as identified in Table 1 was pulverized and sieved to obtain a carrier of from 16 to 8 mesh, and 5 ml of the carrier thus obtained was evacuated at 300° C. for two hours. Then, to this carrier, a vapor of tantalum pentaethoxide was contacted together with dried air at 100° C. under atmospheric pressure for 5 hours. Further, the carrier was evacuated at 300° C. for two hours, and then it was heat treated under a dried air stream at 300° C. for two hours.

Using the catalyst prepared as described above, the reaction was conducted under the same conditions as in Example 1. The results of the reaction upon expiration

COMPARATIVE EXAMPLES 4 TO 7

Catalysts were prepared in the same manner as in Example 1 except that carriers as identified in Table 5 were used instead of the silica in Example 1, and the reaction was conducted in the same manner. The results of the reaction upon expiration of one hour from the initiation of the reaction are shown in Table 5.

TABLE 5

| Comparative Example No. | Carrier | Supported amount of tantalum (wt %) | Conversion of oxime (%) | Selectivity of lactam (%) | Yield of lactam (%) |
|---|---|---|---|---|---|
| 4 | Alumina 1) | 4.5 | 73.2 | 74.1 | 54.2 |
| 5 | Titanium oxide 2) | 3.8 | 60.2 | 44.5 | 26.8 |
| 6 | Magnesium oxide 3) | 4.0 | 43.5 | 74.1 | 32.2 |
| 7 | Silica alumina (alumina: about 20 | 4.2 | 82.1 | 78.8 | 64.7 |

TABLE 5-continued

| Comparative Example No. | Carrier wt % | Supported amount of tantalum (wt %) | Conversion of oxime (%) | Selectivity of lactam (%) | Yield of lactam (%) |
|---|---|---|---|---|---|

1) Alumina: catalyst acedemic society reference catalyst JRC-ALO-1
Total pore volume of pores with diameters of from 40 to 150,000 Å: 0.707 cc/g .. ①
Pore volume of pores with diameters of from 40 to 2,000 Å: 0.610 cc/g ... ②
(②/①) × 100: 86.3%
Peak of the pore diameter: 106 Å
Specific surface area: 160 m²/g
2) Titanium oxide: catalyst academic society reference catalyst JRC-TIO-5
3) Magnesium oxide: catalyst acedemic society reference catalyst JRC-MGO-1
4) Silica-alumina: N631, manufactured by Nikki Kagaku K.K.

COMPARATIVE EXAMPLE 8

To 250 ml of a dry ethanol solution containing 10% by weight of tantalum pentachloride, 250 ml of an ethanol solution of 2N potassium hydroxide was gradually dropwise added, and the mixture was left to stand still for one day. The precipitate thereby obtained was recovered by centrifugal separation. Then, one liter of a 1N hydrochloric acid aqueous solution was added, and the precipitate was dispersed. The dispersion was heated and boiled for one hour, then cooled to room temperature and subjected to centrifugal separation. Then, the same treatment with a 1N hydrochloric acid aqueous solution was repeated. Then, similar treatment was repeated three times by using deionized water instead of the 1N hydrochloric acid aqueous solution. The precipitate thus obtained was dried under reduced pressure at 120° C. for 6 hours and then heat-treated at 300° C. for two hours under a dried air stream.

Using the hydrated tantalum oxide thus obtained, as a catalyst, the reaction was conducted under the same reaction conditions as in Example 1. The results of the reaction are shown in Table 6.

COMPARATIVE EXAMPLE 9

Hydrated niobium oxide (AD382, manufacturered by CBMM International Company) was heat-treated at 300° C. for two hours under a dried air stream. Using this as a catalyst, the reaction was conducted under the same conditions as in Example 1. The results of the reaction are shown in Table 6.

COMPARATIVE EXAMPLE 10

Using acid type mordenite zeolite (catalyst academic society reference catalyst JRC-ZHM20) as a catalyst, the reaction was conducted under the same reaction conditions as in Example 1. The results of the reaction are shown in Table 6.

COMPARATIVE EXAMPLE 11

To an alumina catalyst (catalyst academic society reference catalyst JRC-ALO-1), a vapor of triethoxyborane was contacted together with dried air under an atmospheric pressure at 200° C. for 5 hours and then evacuated at 300° C. for two hours and then further heat-treated at 300° C. for two hours under a dried air stream.

Using a white alumina-carried boron catalyst (supported amount of boron: 26.5 wt % as $B_2O_3$) thus obtained, a reaction was conducted under the same reaction conditions as in Example 1. The results of the reaction are shown in Table 6. Further, after completion of the reaction for 10 hours, the catalyst withdrawn from the reaction tube was colored black, and deposition of carbon was observed.

TABLE 6

| Comparative Example No. | Catalyst | Time passed after initiation of the reaction (hr) | Conversion of oxime (%) | Selectivity of lactam (%) | Yield of lactam (%) |
|---|---|---|---|---|---|
| 8 | Hydrated tantalum oxide | 1 | 42.6 | 69.9 | 29.8 |
| 9 | Hydrated niobium oxide | 1 | 21.2 | 67.5 | 14.3 |
| 10 | Acid type mordenite zeolite | 1 | 42.5 | 63.4 | 26.9 |
| 11 | Boron-supporting alumina carrier | 1 | 93.4 | 92.1 | 86.0 |
|   |   | 10 | 61.5 | 87.6 | 53.9 |

By the method of the present invention employing the Beckmann rearrangement reaction in a gas phase, the desired lactam can be produced at high selectivity without formation of by-product ammonium sulfate.

I claim:

1. A method for preparing a lactam, which comprises subjecting a cycloalkanone oxime to a Beckmann rearrangement reaction in a gas phase in the presence of a carrier-supported catalyst containing tantalum, wherein the carrier-supported catalyst is the one prepared by contacting an organic compound containing tantalum to a silica carrier having pores with pore diameters of from 40 to 150,000 Å wherein the pore volume of pores with pore diameters of from 40 to 2,000 Å is at least 80% of the total pore volume of pores with pore diameters of from 40 to 150,000 Å.

2. The method according to claim 1, wherein the total pore volume of the silica carrier is from 0.1 to 5 cc/g.

3. The method according to claim 1, wherein the pore volume of pores with pore diameters of from 40 to 2,000 Å is at least 90% of the total pore volume of pores of the silica carrier.

4. The method according to claim 1, wherein the peak in the pore size distribution of pores in the silica carrier is within a range of from 100 to 600 Å in diameter.

5. The method according to claim 1, wherein the organic compound containing tantalum is tantalum alkoxide.

6. The method according to claim 1, wherein the organic compound containing tantalum is contacted in the form of a solution to the silica carrier.

7. The method according to claim 1, wherein the organic compound containing tantalum is contacted in the form of a vapor to the silica carrier.

8. The method according to claim 1, wherein the carriersupported catalyst contains tantalum in an amount of from 1 to 30 wt % as $Ta_2O_5$.

9. The method according to claim 1, wherein the cycloalkanone oxime is cyclohexanone oxime.

* * * * *